(12) United States Patent
Boderke et al.

(10) Patent No.: US 10,967,036 B2
(45) Date of Patent: Apr. 6, 2021

(54) COMPOSITION COMPRISING AN ONION EXTRACT AND LIPOSOMES

(71) Applicant: MERZ PHARMA GmbH & CO. KGaA, Frankfurt am Main (DE)

(72) Inventors: Peter Boderke, Schwalbach (DE); Martina Heberer, Heusenstamm (DE); Petra Scheppler, Mainz (DE)

(73) Assignee: HRA Pharma, Chatillon (FR)

( * ) Notice: Subject to any disclaimer, the term of this patent is extended or adjusted under 35 U.S.C. 154(b) by 412 days.

(21) Appl. No.: 15/725,485

(22) Filed: Oct. 5, 2017

(65) Prior Publication Data

US 2018/0028587 A1    Feb. 1, 2018

Related U.S. Application Data

(63) Continuation of application No. 14/128,190, filed as application No. PCT/EP2012/061997 on Jun. 21, 2012, now abandoned.

(60) Provisional application No. 61/571,287, filed on Jun. 24, 2011.

(30) Foreign Application Priority Data

Jun. 24, 2011   (EP) ..................... 11171378

(51) Int. Cl.
| | | |
|---|---|---|
| *A61K 36/88* | (2006.01) | |
| *A61K 9/00* | (2006.01) | |
| *A61K 47/10* | (2017.01) | |
| *A61K 36/8962* | (2006.01) | |
| *A61K 9/06* | (2006.01) | |
| *A61K 9/127* | (2006.01) | |

(52) U.S. Cl.
CPC ............ *A61K 36/88* (2013.01); *A61K 9/0019* (2013.01); *A61K 9/06* (2013.01); *A61K 9/127* (2013.01); *A61K 9/1277* (2013.01); *A61K 36/8962* (2013.01); *A61K 47/10* (2013.01); *A61K 2236/00* (2013.01)

(58) Field of Classification Search
None
See application file for complete search history.

(56) References Cited

U.S. PATENT DOCUMENTS

| | | |
|---|---|---|
| 5,124,167 A | 6/1992 | Albeck |
| 5,165,932 A | 11/1992 | Horvath |
| 5,321,045 A | 7/1994 | Dorsch |
| 5,885,581 A | 3/1999 | Massand |
| 2008/0318325 A1 | 12/2008 | Blume et al. |
| 2010/0247689 A1 | 9/2010 | Paspaleeva-Kühn |

FOREIGN PATENT DOCUMENTS

| | | |
|---|---|---|
| CN | 1522150 A | 8/2004 |
| CN | 1660121 A | 8/2005 |
| CN | 101297906 A | 11/2008 |
| DE | 3723248 | 7/1987 |
| DE | 102008032327 | 1/2010 |
| DE | 102009028996 | 3/2011 |
| EP | 0 201 956 | 11/1986 |
| EP | 0 364 442 | 4/1990 |
| EP | 0429 080 | 5/1991 |
| WO | Wo 2006/068759 | 6/2006 |
| WO | WO2006068759 | 6/2006 |
| WO | WO2007003538 | 1/2007 |
| WO | WO2010092142 | 8/2010 |
| WO | WO 20111006100 | 1/2011 |

OTHER PUBLICATIONS

Draelos (2008) Journal of Cosmetic Dermatology, 7, 101-104. (Year: 2008).*
Perez et al. (2010) Journal of Drugs in Dermatology, vol. 9, Issue 5, 514-518. (Year: 2010).*
Fang, Jia-You, et al., "Enhancement of the transdermal delivery of catechins by liposomes inforporating anionic surfactants and ethanol", International Journal of Pharmaceutics, 310, 2006, pp. 131-138.
Korean Search Report for KR10-2014-7001883 dated Jan. 10, 2019.
International Search Report With Written Opinion dated Jul. 31, 2012 for PCT/EP2012/061997.
Campanati, Anna, et al., "Effect of allium cepa-allantoin-pentaglycan gel on skin hypertrophic scars: clinical and video-capillaroscopic results of an open-label, controlled, nonrandomized clinical trial", Dermatol. Surg. e6. 2010, 1439-1444.
Draelos, et al. "A New Propriatary Onion Extract Gel Improves the Appearance of New Scars", Clinical and Aesthetic Dermatology, vol. 5(6), pp. 18-24, Jun. 2012.
Fang, Jia-You, et al., "Enhancement of the transdermal delivery of catechins by liposomes incorporating anionic surfactants and ethanol", International Journal of Pharmaceuticals, 310, 2006, 131-138.
Lautenschlaeger, Hans, "Liposomes", Handbook of Cosmetic Science and Technology (2nd Edition), 2006, 155-163.

(Continued)

*Primary Examiner* — Russell G Fiebig
(74) *Attorney, Agent, or Firm* — Hueschen and Sage

(57) ABSTRACT

The present invention relates to a composition comprising a first onion extract (A), and liposomes, wherein at least a portion of the onion extract is encapsulated in the liposomes. Furthermore the present invention relates to a method for preparing a composition comprising a first onion extract (A), and liposomes, wherein at least a portion of the onion extract is encapsulated in the liposomes. Further, the present invention relates to a composition comprising an onion extract (A) (*Allium cepa*) and liposomes, obtainable by or obtained by the method. Furthermore, the present invention relates to compositions comprising a first onion extract (A), and liposomes, wherein at least a portion of the onion extract is encapsulated in the liposomes, for use in treating and/or preventing scars.

11 Claims, No Drawings

(56) References Cited

OTHER PUBLICATIONS

Nuutila, Anna Maria, et al., "Comparison of antioxidant activities of onion and garlic extracts by inhibition of lipid peroxidation and radical scavenging activity", Food Chemistry 81, 2003, 485-493.

Saleheen, Danish, et al, "Antileishmanial activity of aqueous onion extract in vitro", Fitoterapia, 75, 2004, 9-13.

Tassin, Severine, et al., "Solution structure of Ace-AMP1, a potent antimicrobial protein extracted from onion seeds. Structural analogies with plant nonspecific lipid transfer proteins", Biochemistry 37, 1998, 3623-3637.

Touitou, E., et al "Liposomes as carriers for topical and transdermal delivery", Journal of Pharmaceutical Sciences, vol. 83, No. 9, 1994, 1180-1203.

Ulrich, Anne S., "Biophysical aspects of using liposomes as delivery vehicles", Bioscience Report, vol. 22. No. 2, Apr. 2002, 129-150.

Verma, D.D., et al., "Particle size of liposomes influences dermal delivery of substances into skin". Intern. J. Pharmaceutics, 258, 2003, 141-151.

De Leeuw, et al., "Liposomes in dermatology today", Journal of the European Academy of Dermatology and Venerology, 23:505-516, 2009.

Egbaria et al., "Liposomes as a topical drug delivery system", Advanced Drug Delivery Reviews, 5:287-300, 1990.

Foldvari, et al, "Dermal drug delivery by liposome encapsulation: Clinical and electron microscopic studies", J. Microencapsulation, vol. 7, No. 4, 1990, pp. 479-489.

Honeywell-Nguyen, et al., "Vesicles as a tool for transdermal and dermal delivery", Drug Discovery Today: Technologies, Drug delivery/formulation and nanotrechnology, vol. 2, No. 1, 2005, pp. 67-74.

Schmid, et al., "Liposomes: A drug carrier system for topical treatment in dermatology" Critical Reviews in Therapeutic Drug Carrier Systems, 11(2&3): 1994, pp. 97-118.

Yarosh, DB, "Topical application of liposomes", Journal of Photochemistry and Photobiology B: Biology, vol. 6, Issue 4, Aug. 1990, pp. 445-449.

* cited by examiner

US 10,967,036 B2

COMPOSITION COMPRISING AN ONION EXTRACT AND LIPOSOMES

The present invention relates to a composition comprising a first onion extract (A), and liposomes, wherein at least a portion of the onion extract is encapsulated in the liposomes. Furthermore the present invention relates to a method for preparing a composition comprising a first onion extract (A), and liposomes, wherein at least a portion of the onion extract is encapsulated in the liposomes. Further, the present invention relates to a composition comprising an onion extract (A) (*Allium cepa*) and liposomes, obtainable by or obtained by said method. Furthermore, the present invention relates to compositions comprising a first onion extract (A), and liposomes, wherein at least a portion of the onion extract is encapsulated in the liposomes, for use in treating and/or preventing scars Scars are areas of fibrous tissue that replace normal skin after injury. A scar results from the biological process of wound healing in the skin and other tissues of the body. With the exception of very minor lesions, every wound (e.g. after accident, disease, or surgery) results in some degree of scarring.

Thus, a scar is an end product of a wound healing process. This end product is neither aesthetically nor functionally perfect. Unwounded dermis comprises a mechanically efficient meshwork of collagen. However, wound healing in human skin results in varying degrees of scar formation, ranging clinically from fine asymptomatic scars to problematic hypertrophic and keloid scars, which may limit function, restrict further growth. In addition they may have a poor cosmetic appearance.

Treatment options for scars range from invasive procedures and surgery such as excision or laser therapy to non-invasive management, in particular administration of topical agents. Moreover, scars frequently remain untreated.

Agents for treating scars are known in the art.

For example, the product Kelofibrase® is known a scar cream which comprises, as active ingredient, urea and heparin sodium (60 000 I.U.) and camphor as well as customary oil/emulsifier components. This product is reportedly useful for scar treatment, for scar contractures and keloids. Here, heparin-sodium acts, as is known, as a blood-thinning agent.

Under the name Hirudoid®forte is known a gel which comprises, as active ingredient, mucopolysaccharide polysulfuric ester (445 mg, corresponding to 40 000 units in 100 g of ointment). Further ingredients are the components required for the preparation of the gel, such as isopropyl alcohol, polyacrylic acid, propylene glycol and water. Mucopolysaccharide polysulfuric esters generally have a heparinoid effect and therefore correspond to the Kelofibrase® product specified above. As well as the gel, a Hirudoid®forte ointment is also known which, as well as the abovementioned active ingredients, has a mixture of monoglycerides and diglycerides with higher fatty acids and medium-chain triglycerides etc., and isopropyl alcohol, imide urea, phenoxyethanol and water. Products of this type can be used for treatment in cases of phlebopathies, superficial phlebitides, hematomas and for loosening hard scars. The product must not be applied to damaged skin.

Under the name Hylaform® is known a gel implant which contains crosslinked hyaluronic acid which is present in an aqueous sodium-chloride-containing solution for the purpose of injection. Using such an agent, skin deformations are said to be treatable. However, acute or chronic skin disorders in the affected correction area must not be present.

Under the name Linoladiol® N is known a hydrophilic O/W cream which comprises estradiol as active ingredient in the cream base. By means of this hormone-containing preparation, as well as gynecological applications, dermatological applications, such as burns, scar treatment, atrophy of the skin, perioral dermatitis and eczema in the acute and subacute stage are also stated. In this connection, however, the application limitations known for hormone-containing products, such as side effects and/or interactions, are to be taken into consideration to a considerable degree.

Further some products for use in treating or preventing scar formation which comprise plant extracts as active ingredients are described.

In particular, gel-like products are used for this purpose. U.S. Pat. No. 5,885,581 describes such a gel-like product which comprises 20-30% by weight of polyethylene glycol 200, 0.005-0.03% by weight of preservative, 0.05-0.2% by weight of sorbic acid, 0.5-2% by weight of allantoin, 1-3% by weight of xanthan and, if desired, perfume substances and which is characterized by 5-15% by weight of a liquid onion extract (*Allium cepa* extract), based on an aqueous carrier in an amount of about 55-65% by weight. The product thus represents a fat (oil)-free gel and is applied externally to damaged skin tissue, in particular scarred tissue. The product is further characterized by a pH of 4.5-5.5 and a particle size of less than 50 um.

Under the product name Contractubex® a gel is known which comprises an onion extract (*Allium cepa* extract). Onion extracts for the treatment of scars are also disclosed in US2010/0247689.

The product name PC 30 V describes a liquidum which comprises horse chestnut seed dry extract and also chamomile blossom dry extract in 1,3-butanediol, dexpanthenol, allantoin and odor substances. This agent is said to be useful in the treatment of skin damage, such as wound chafing of sensitive pressure points and scars by orthopedic apparatuses, and also pressure sores. An indication with regard to scars as a result of operations or other skin damage is not stated here.

WO 2011/006100 discloses corticosteroids for reducing scar formation.

DE-A 37 23 248 relates to the use of thiosulfinic acid derivatives for the treatment of inflammations. These may be obtained, inter alia, by extraction from onions and subsequent chromatography. Onion extract itself is not used here.

EP-B 429 080 relates to a preparation process for S-allylcysteine-containing products, where, for example, aqueous garlic extracts are admixed with cysteine, giving S-allylcysteine.

EP-B 364 442 relates to an oil extract from at least 3 different herbs chosen from euphorbia, veronica, yarrow, fumitory, garlic, nettle and marigold. This combination is used in the form of an oil, e.g. with paraffin, against psoriasis. [0017] EP-B EP 201 956 relates to the extraction and chromatographic fractionation, for example, of tobacco, algae, garlic, where the specific substances obtained are reportedly There however remains the need for advantageous agents for scar treatment.

SUMMARY OF THE INVENTION

The present invention relates to a composition comprising a first onion extract (A), and liposomes, wherein at least a portion of the onion extract is encapsulated in the liposomes.

Furthermore the present invention relates to a method for preparing a composition, and a composition obtainable or obtained by said method, the composition comprising a first onion extract (A), and liposomes, wherein at least a portion of the first onion extract (A) is encapsulated in the liposomes, said method comprising:
(i) providing a first onion extract (A)
(ii) providing liposomes, and
(iii) contacting the first onion extract (A) according to (i) with the liposomes according to (ii), thereby encapsulating at least a portion of the first onion extract (A) into liposomes.

In a further aspect, the present invention relates to a composition, as described above for use in treating and/or preventing scars.

Furthermore, the present invention relates to a method for treating and/or preventing scars fin a subject in need thereof comprising administering to said subject a therapeutically effective amount of a composition, as described above.

DETAILED DESCRIPTION

Therefore, in a first aspect, the present invention concerns a composition comprising a first onion extract (A), and liposomes, wherein at least a portion of the onion extract is encapsulated in the liposomes.

The present invention also relates to such a composition further comprising a second onion extract (B), wherein the first onion extract (A) comprises a higher concentration of onion components compared to the second onion extract (B).

It was surprisingly found that a stable composition comprising a high concentration of an onion extract, thus of the active ingredient, can be provided by encapsulating at least a portion of the first onion extract. Further, it is contemplated that the liposomes which act as delivery system are capable of transporting the encapsulated active ingredients into deeper layers of the skin thereby providing improved cosmetic benefits and a controlled release of the onion extract.

Without wishing to be bound by theory, it is further believed that encapsulating at least a portion of the first onion extract (A), in particular if the onion extract comprises onion components in high concentrations, positively influences the stability of such a composition.

Liposomes:

Within the meaning of the present invention, the term "liposome" is denoted to mean an artificially prepared vesicle made of at least one lipid bilayer (lipid membrane), wherein the liposome comprises naturally-derived or synthetic phospholipids or other surfactants, and optionally other membrane components such as cholesterol and proteins, which structure can act as a physical reservoir for active ingredients such as for the first onion extract (A), as described above.

Preferably the liposome according to the invention is a phospholipid comprising liposome, i.e. a liposome comprising at least one naturally-derived or synthetic phospholipid. Optionally the phospholipid-comprising liposome according to the invention comprises further membrane components such as cholesterol and proteins.

Thus, the present invention also relates to a composition, as described above, wherein the liposomes are phospholipid-comprising liposomes. Likewise, the present invention relates to a method for preparing a composition, as described above, and a composition obtainable or obtained by said method, wherein the liposomes are phospholipid comprising liposomes.

Within the meaning of the present invention the term "phospholipid" refers to a lipid or glyceride that contains a phosphate group. Thus the phospholipid may be, for example, lecithin, phosphatidyl ethanolamine, phosphatidyl inositol, phosphatidyl serine, diphosphatidyl glycerol (cardiolipin), dilauroyl phosphatidyl choline, dimyristoyl phosphatidyl choline, dipalmitoyl phosphatidyl choline, distearoyl phosphatidyl choline, dioleoyl phosphatidyl choline, dimyristoyl phosphatidyl ethanolamine, dipalmitoyl phosphatidyl ethanolamine, dipalmitoyl phosphatidyl glycerol, dimyristoyl phosphatidic acid, dipalmitoyl phosphatidic acid, dipalmitoyl phosphatidyl serine, dipalmitoyl sphingomyelin, 1-stearic acid-2palmitoyl phosphatidyl choline, polyethylene glycol-2stearoyl phosphatidyl ethanolamine.

Preferably, the liposomes according to the invention are phospholipid comprising liposomes, wherein the amount of phospholipids present in each liposome is preferably at least 50% by weight, more preferably in the range of from 50 to 80% by weight, more preferably in the range of from 55 to 70% by weight and most preferably in the range of from 58 to 65% by weight, based on the total weight of all membrane components forming the liposome (phospholipids, other surfactants, and optionally other membrane components, without any encapsulated solvent or onion extract)

According to a further embodiment of the invention the liposomes according to the invention are lecithin comprising liposomes. Thus, the present invention also relates to a composition, as described above, wherein the liposomes are lecithin comprising liposomes. Likewise, the present invention relates to a method for preparing a composition, as described above, and a composition obtainable or obtained by said method, wherein the liposomes are lecithin comprising liposomes Within the meaning of the present invention the term "lecithin" refers to a naturally occurring or synthetic lecithin, which may be suitably refined. Suitable lecithins include, but are not limited to lecithins derived from egg or soybean. Further suitable lecithins include, but are not limited to dihexanoyl-L-alpha-lecithin, dioctanoyl-L-alpha-lecithin, didecanoyl-L-alpha-lecithin, didodecanoyl-L-alpha-lecithin, ditetradecanoyl-L-alpha-lecithin, dihexadecanoyl-L-alpha-lecithin, dioctadecanoyl-L-alpha-lecithin, dioleoyl-Lalpha-lecithin, dilinoleoyl-L-alpha-lecithin, alpha-palmitol. Lecithins are typically mixtures of diglycerides of fatty acids linked to the choline ester of phosphoric acid, and can contain differing amounts of other compounds depending on the method of isolation. Typically, commercial lecithin is a mixture of acetone-insoluble phosphatides. Preferably, the lecithin is obtained from seeds including soybean and corn, most preferably soybean, using methods well known in the art. Lecithin obtained from soybean is referred to herein as soy bean lecithin.

In other more specific embodiments, the liposomes according to the invention are soy bean lecithine comprising liposomes, wherein the amount of soy bean lecithine present in each liposome is preferably at least 99% by weight, preferably at least 99.9% by weight, based on the total weight of all membrane components forming the liposome (without any encapsulated solvent or onion extract).

As to the soy bean lecithin, said soy bean lecithin typically comprises at least 50% by weight of phospholipids, more preferably of from 50 to 80% by weight, more preferably of from 55 to 70% by weight and most preferably of from 58 to 65% by weight, based on the total weight of the soy bean lecithin.

The soy bean lecithine, as described above, usually comprises phosphatidylcholine, phosphatidylethanolethanolamine, phosphatidylinositol and phosphatidic acid. A typical composition comprises phosphatidylcholine in an amount in the range of from 13 to 18% by weight, phosphatidylethanolethanolamine in an amount in the range of from 10 to 15% by weight, phosphatidylinositol in an amount in the range of from 10 to 15% by weight and phosphatidic acid in an amount in the range of from 5 to 12% by weight, -%, based on the total weight of the soybean lecithin present in the liposome.

The liposomes according to the invention may have e.g. a multilamellar or an unilamellar structure, wherein unilamellar liposomes are preferred.

According to further embodiments of the invention, the average diameter (particle size, herein also referred to as "diameter") of the liposomes is in the range of from 50 to 450 nm, more preferably in the range of from 100 nm to 400 nm and most preferably in the range of from 150 nm to 350 nm, measured by Photon Correlation Spectroscopy (PCS). "Particle Size" or "diameter" refers to the averaged hydrodynamic diameter as measured by Photon Correlation Spectroscopy—also referred to as Dynamic Light Scattering—from diluted solutions. The method is based on the scattering of laser light by particles and utilizes the measurement of the speed at which particles are diffusing due to Brownian motion. The particle velocity correlates to the size of particles. The Photon Correlation Spectroscopy was carried out using a Zetamaster S/ZEM 5002 by means of a 5 mW He—Ne laser (670 nm), with a measuring angle of 90° at a temperature of 25° C.+/−0.5° C.

Thus, the present invention also relates to a composition, as described above, wherein the liposomes have a diameter in the range of from 50 to 450 nm, preferably in the range of from 150 to 350 nm, measured by Photon Correlation Spectroscopy. Likewise, the present invention relates to a method for preparing a composition, as described above, and a composition obtainable or obtained by said method, wherein the liposomes have a diameter in the range of from 50 to 450 nm, preferably in the range of from 150 to 350 nm, measured by Photon Correlation Spectroscopy.

Liposomes suitable for the composition according to the invention are commercially available, e.g. from Rovi cosmetics International GmbH, In yet another embodiment of the invention, the amount of liposomes present in the composition of the invention is in the range of from 0.01 to 0.5% by weight, preferably in the range of from 0.02 to 0.4% by weight, more preferably in the range of from 0.03 to 0.3% by weight, more preferably in the range of from 0.04 to 0.2% by weight, based on the total weight of the composition. The term "amount of liposomes" as used in the context of the invention refers to the sum of all membrane components forming the liposome (phospholipids, other surfactants, and optionally other membrane components, without any encapsulated solvent or onion extract).

The First Onion Extract (A)

As used herein, the term "onion" refers to any *Allium* species including, but not limited to, *Allium cepa, Allium fistulosum, Allium schoenoprasmn, Allium ascalonicufn, Allium cernuu,* and *Allium ampeloprasum.* Thus, as used herein, the term "onion" means any type of onion including, but not limited to, any cultivated onion, any wild onion, any onion species, any intra- and inter-species onion crosses, all onion varieties, all onion genotypes and all onion cultivars.

Preferably, the extracts are obtained from the bulbs of the onion. According to a preferred embodiment, the first onion extract (A) is an *Allium cepa* extract.

Thus, the present invention also relates to a composition, as described above, wherein the first onion extract (A) is an *Allium cepa* extract. Likewise, the present invention relates to a method for preparing a composition, as described above, and a composition obtainable or obtained by said method, wherein the first onion extract (A) is an *Allium cepa* extract.

According to further embodiments of the invention, the amount of the first onion extract (A), preferably the first *Allium cepa* extract (A), present in the composition according to the invention, is in the range of from 0.1 to 25% by weight, more preferably in the range of from 0.2 to 20% by weight, more preferably in the range of from 0.3 to 15% by weight, more preferably in the range of from 0.4 to 12% by weight, more preferably in the range of from 0.5 to 10% by weight, and most preferably in the range of from 0.5 to 3% by weight, such as 0.5, 0.6, 0.7, 0.8, 0.9, 1.0, 1.1, 1.2, 1.3, 1.4, 1.5, 1.6, 1.7, 1.8, 1.9, 2.0, 2.1, 2.1, 2.3, 2.4, 2.5, 2.6, 2.7, 2.8, 2.9 or 3.0% by weight, based on the total weight of the composition.

The term "onion extract" as used herein means a substance or composition obtained from an onion which is obtained by extraction, maceration or percolation of the onion material with a suitable solvent and, optionally, by partial or complete removal of the solvent. Thus, extracts in accordance with this invention are either so-called solvent-processed fluid extracts or so called dry onion extracts obtained by evaporation of the whole liquid extract to dryness, e.g. by air drying, spray drying, vacuum oven drying, fluid-bed drying or freeze-drying, and optional washing and/or re-dissolving of this dry extract in at least one suitable solvent. Solvents suitable for extraction, percolation or maceration are known to those experienced in the art. Acetone, chloroform, ethyl acetate, lower alkanols with 1 to 4 carbon atoms, alcohols or a mixture of these and water are particularly suited. Carbon dioxide in fluid or super-critical form and pressurized gases with solvent properties are also suitable as extraction agents.

According yet another embodiment the first onion extract (A) comprises a solvent $S_2$, wherein said solvent is either the solvent used for extraction, maceration or percolation of the onion material or a solvent used for re-dissolving the dry extract.

In further embodiments of the foregoing, $S_2$ comprises at least one alcohol and water. As to the at least one alcohol, this alcohol is preferably selected from the group consisting of ethanol, propanol, iso-propanol or mixtures thereof. Most preferably, the at least one alcohol is ethanol.

Thus, the present invention also relates to a composition, as described above, wherein the first onion extract (A) comprises a solvent $S_2$, said solvent comprising at least one alcohol, preferably ethanol, and water. Likewise, the present invention relates to a method for preparing a composition, as described above, and a composition obtainable or obtained by said method, wherein the first onion extract (A) comprises a solvent $S_2$, said solvent comprising at least one alcohol, preferably ethanol, and water.

In further embodiments of the invention, the solvent $S_2$ comprises water in an amount in the range of from 95 to 75% by weight, preferably in the range of from 90 to 84% by weight, and most preferably in the range of from 92 to 82% by weight, based on the total weight of the solvent $S_2$. As described above, the solvent $S_2$ comprises the at least one alcohol, wherein said at least one alcohol is preferably present in the range of from 5 to 25% by weight, preferably in the range of from 8 to 18% by weight, and most preferably in the range of from 10 to 16% by weight, based on the total weight of the solvent $S_2$.

Preferably $S_2$ comprises ethanol in an amount in the range of from 5 to 25% by weight and water in an amount of from 95 to 75% by weight, more preferably ethanol in an amount in the range of from 8 to 18% by weight and water in an amount of from 92 to 82% by weight, and most preferably ethanol in an amount in the range of from 10 to 16% by weight and water in an amount of from 90 to 84% by weight.

Thus, the present invention also relates to a composition, as described above, wherein the first onion extract (A) comprises a solvent $S_2$, wherein $S_2$ comprises ethanol in an amount in the range of from 5 to 25% by weight and water in an amount of from 95 to 75% by weight, based on the total weight of the solvent $S_2$. Likewise, the present invention relates to a method for preparing a composition, as described above, and a composition obtainable or obtained by said method, wherein the first onion extract (A) comprises a solvent $S_2$, wherein $S_2$ comprises ethanol in an amount in the range of from 5 to 25% by weight and water in an amount of from 95 to 75% by weight, based on the total weight of the solvent $S_2$.

$S_2$ may optionally comprise further organic solvents such as, for example, isopropanol or methanol. Preferably $S_2$ comprises less than 0.1% by weight of further organic solvents in total, preferably less than 0.05% by weight, based on the total weight of the solvent $S_2$. As to the amount of onion components present in the first onion extract, these components are preferably present in an amount of 20 to 33% by weight, preferably 25 to 30 by weight, based on the total amount the first onion extract (A), wherein this amount refers to the weight of the dry onion extract, before dissolving this dry onion extract in the Solvent $S_2$.

According to a further embodiment of the invention, the first onion extract (A) is an onion extract which is obtained or obtainable by a process comprising an extraction, maceration or percolation of the onion material, either of fresh or dried onions, with a suitable solvent $S_1$ and a subsequent partial or preferably complete removal of the solvent. According to a preferred embodiment of the invention, after complete removal of the solvent, the remaining residue is re-dissolved in at least one suitable solvent, preferably in the above described solvent $S_2$.

Optionally, the process for preparing the first onion extract (A) may comprise further steps, such as purification steps, in particular filtration steps.

As to the solvent $S_1$ used in the process, described above, any suitable solvent may be used. Thereby, $S_1$ may be the same or may differ from the above described solvent $S_2$. Preferably, $S_1$ comprises at least one alcohol. As to the at least one alcohol, this alcohol is preferably selected from the group consisting of ethanol, propanol, iso-propanol or mixtures thereof. Most preferably, the at least one alcohol comprised in $S_1$ is ethanol.

According to an embodiment of the foregoing, the least one alcohol is present in an amount of at least 70% by weight, preferably of at least 80% by weight, more preferably of at least 90% by weight, and most preferably of at least 96% by weight, based on the total weight of the solvent $S_1$.

$S_1$ may optionally comprise water and/or further organic solvents such as, for example, isopropanol or methanol. Preferably $S_1$ comprises less than 0.1% by weight of further organic solvents in total, preferably less than 0.05% by weight, based on the total weight of the solvent $S_1$. In particular, $S_1$ comprises water in an amount of less than 30% by weight, preferably of less than 20% by weight, more preferably of less than 10% by weight, and most preferably of less than 4% by weight.

According to an alternative embodiment of the invention $S_1$ comprises ethanol in an amount in the range of from 5 to 25% by weight and water in an amount of from 95 to 75% by weight, more preferably ethanol in an amount in the range of from 8 to 18% by weight and water in an amount of from 92 to 82% by weight, and most preferably ethanol in an amount in the range of from 10 to 16% by weight and water in an amount of from 90 to 84% by weight.

According to a further embodiment of the invention, fresh or dried onions or parts of onions, such as onion chips, are extracted with a solvent $S_1$, as described above, comprising at least one alcohol to give a liquid phase $L_1$ and a solid residue $R_0$, or a composition consisting of the liquid phase $L_1$ and the solid residue $R_0$.

In yet another embodiment of the foregoing, the ratio of amount of onion (weight) to solvent $S_1$ (weight) is in the range of from 0.5:0.9 to 0.7:1, more preferably in the range of about 0.65:1.

The extraction can be carried out in one or more extraction steps. Preferably a multi-stage extraction is carried out in which a multiplicity of separating stages connected in series is used.

After the extraction, described above, the liquid phase ($L_1$) is preferably separated from the solid residue ($R_o$).

Between the separation step and the extraction step, the liquid phase $L_1$ and the solid residue $R_o$ is preferably allowed to stand for a time in the range of from 1 h to 4 weeks, preferably in the range of from 1 day to 3 weeks, more preferably about 1 to 2 weeks, in particular at a temperature in the range of from 10 to 40° C., more preferably at a temperature in the range of from 10 to 30° C., most preferably at room temperature. Thereby, further solid residue $R_o$ may precipitate from the liquid phase $L_1$.

The separation step may be carried out by any suitable method known to those skilled in the art. According to one embodiment of the invention, the separation is carried out by filtration. The term "filtration" or "filtering" refers to the process of removing essentially all, preferably all, of the solid residue $R_o$, which may be present as suspended particles, from the liquid phase by passing the composition through one or more membranes or filters.

The liquid phase $L_1$ obtained is subsequently, optional after further purification steps, concentrated, preferably evaporated to dryness as mentioned above, to give residue $R_1$. Optionally, the liquid phase $L_1$ obtained is allowed to stand for a time in the range of from 1 h to 4 weeks, preferably in the range of from 1 day to 3 weeks, more preferably about 1 to 2 weeks, in particular at a temperature in the range of from 10 to 40° C., more preferably at a temperature in the range of from 10 to 30° C., most preferably at room temperature. Thereby, further solid residue may precipitate from the liquid phase $L_1$. In case further precipitates are formed, preferably at least one filtration is carried out.

In the preferred case in which $L_1$ is evaporated to dryness, the residue $R_1$ corresponds to the dry onion extract mentioned above.

Subsequent to the evaporating step, the method may comprise further steps, such as, e.g. at least one purification step and/or at least one homogenization step. Preferably, the residue $R_1$, more preferably the dry onion extract $R_1$, is at least homogenized.

As described above, residue $R_1$, preferably the homogenized residue $R_1$ is preferably re-dissolved in the above-described solvent $S_2$, with $S_2$ preferably comprising at least one alcohol and water, to give the first onion extract (A).

According to a further embodiment of the invention, the first onion extract (A) comprises the solvent $S_2$ in an amount in the range of from 67 to 80% by weight, preferably in the range of from 70 to 75% by weight, more preferably in the range of from 70 to 72% by weight, based on the total weight of the first onion extract (A). Further, the first onion extract (A) preferably comprises the residue $R_1$ in an amount in the range of from 20 to 33% by weight, preferably in the range of from 25 to 30% by weight, more preferably in the range of from 28 to 30% by weight, based on the total weight of the first onion extract (A).

In yet another embodiment of the invention, the first onion extract (A) consists of 20 to 33% by weight of residue $R_1$ and 67 to 80% by weight of the solvent $S_2$, preferably of 25 to 30% by weight of residue $R_1$ and 70 to 75% by weight of the solvent $S_2$, and most preferably of 28 to 30 % by weight of residue $R_1$ and 70 to 72% by weight of the solvent $S_2$, based on the total amount of the onion extract (A), with the sum of the amounts of $R_1$ and $S_2$ giving 100% by weight.

Thus, according to a further embodiment, the first onion extract (A) is an onion extract obtained or obtainable by a process comprising the steps
(a) extracting fresh or dried onions, preferably *Allium cepa*, with a solvent $S_1$ comprising at least one alcohol to give a liquid phase $L_1$ and a solid residue $R_o$
(b) separating the liquid phase $L_1$ from the solid residue $R_o$
(c) evaporating the liquid phase $L_1$ to give a residue $R_1$
($d_A$) redissolving the residue $R_1$ in a solvent $S_2$ comprising at least one alcohol and water to give the first onion extract (A)
wherein the first onion extract (A) comprises $R_1$ in an amount of 20 to 33% by weight, based on the total weight of the first onion extract (A).

As described above, at least a portion of the first onion extract (A) is encapsulated in the liposomes. The term "encapsulated" means that the (portion of) the onion extract (A) is enclosed within the liposomes.

Within the meaning of the present invention, the term "at least a portion of the first onion extract (A)" is denoted to mean that at least 20% by weight, preferably at least 22% by weight, more preferably at least 24% by weight, more preferably at least 26% by weight, more preferably at least 27% by weight, more preferably 28 to 40%, and more preferably 29 to 35%, and more preferably 29 to 31% by weight, based on the total weight of the first onion extract (A), is encapsulated in the liposomes.

The Second Onion Extract (B)

According to a further embodiment of the invention, the composition comprises besides the first onion extract (A), additionally a second onion extract (B), wherein the nature of the onion used to prepare the extract (B) may be the same or may differ from the onion used to prepare the onion extract (A).

According to a preferred embodiment, the second onion extract (B) is an *Allium cepa* extract.

Thus, the present invention also relates to a composition, as described above, wherein the composition comprises besides the first onion extract (A), additionally a second onion extract (B), wherein the second onion extract (B) is an *Allium cepa* extract. Likewise, the present invention relates to a method for preparing a composition, as described above, and a composition obtainable or obtained by said method, wherein the composition comprises besides the first onion extract (A), additionally a second onion extract (B), wherein the second onion extract (B) is an *Allium cepa* extract.

According to one embodiment of the invention, the first onion extract (A) as well as the second onion extract (B) are both *Allium cepa* extracts.

In a further embodiment of the invention, the amount of the second onion extract (B), preferably the second *Allium cepa* extract (B), present in the composition according to the invention, is in the range of from 0.1 to 25% by weight, more preferably in the range of from 0.1 to 25% by weight, more preferably in the range of from 1 to 20% by weight, more preferably in the range of from 2 to 18% by weight, more preferably in the range of from 3 to 17% by weight, and most preferably in the range of from 5 to 15% by weight, such as 5, 6, 8, 7, 9, 10 11, 12, 13 or 14% by weight, based on the total weight of the composition. According to a preferred embodiment the second onion extract (B) comprises a solvent $S_3$, wherein said solvent is either the solvent used for extraction, maceration or percolation of the onion material or a solvent used for re-dissolving the dry extract.

Preferably $S_3$ comprises at least one alcohol and water. As to the at least one alcohol, this alcohol is preferably selected from the group consisting of ethanol, propanol, iso-propanol or mixtures thereof. Most preferably, the at least one alcohol is ethanol.

Thus, the present invention also relates to a composition, as described above, wherein the composition comprises besides the first onion extract (A), additionally a second onion extract (B), and wherein the second onion extract (B) comprises a solvent $S_3$, said solvent comprising at least one alcohol, preferably ethanol, and water. Likewise, the present invention relates to a method for preparing a composition, as described above, and a composition obtainable or obtained by said method, wherein the composition comprises besides the first onion extract (A), additionally a second onion extract (B), and wherein the second onion extract (B) comprises a solvent $S_3$, said solvent comprising at least one alcohol, preferably ethanol, and water.

According to another embodiment of the invention, the solvent $S_3$ comprises water in an amount in the range of from 60 to 95% by weight, preferably in the range of from 70 to 90% by weight, more preferably in the range of from 70 to 85% by weight, preferably in the range of from 70 to 80% by weight, and most preferably in the range of from 75 to 80% by weight, based on the total weight of the solvent $S_3$.

As described above, the solvent $S_3$ comprises the at least one alcohol, wherein said at least one alcohol is preferably present in an amount in the range of from 5 to 40% by weight, preferably in the range of from 10 to 30% by weight, more preferably in the range of from 15 to 30% by weight, preferably in the range of from 20 to 30% by weight, and most preferably in the range of from 20 to 25% by weight, based on the total weight of the solvent $S_3$.

Preferably $S_3$ comprises ethanol in an amount in the range of from 5 to 40% by weight and water in an amount of from 95 to 60% by weight, more preferably ethanol in an amount in the range of from 10 to 30% by weight and water in an amount of from 70 to 90% by weight, and most preferably ethanol in an amount in the range of from 20 to 25% by weight and water in an amount of from 75 to 80% by weight.

Thus, the present invention also relates to a composition, as described above, wherein the composition comprises besides the first onion extract (A), additionally a second onion extract (B), and wherein the second onion extract (B) comprises a solvent $S_3$, said solvent comprising ethanol in an amount in the range of from 5 to 40% by weight and water in an amount of from 95 to 60% by weight, based on total weight of the solvent $S_3$. Likewise, the present invention relates to a method for preparing a composition, as described above, and a composition obtainable or obtained by said method, wherein the composition comprises besides the first onion extract (A), additionally a second onion extract (B), and wherein the second onion extract (B) comprises a solvent $S_3$, said solvent comprising ethanol in an amount in the range of from 5 to 40% by weight and water in an amount of from 95 to 60% by weight, based on the total weight of the solvent $S_3$ As to the amount of onion components present in the second onion extract (B), these components are preferably present in an amount of 2 to 15% by weight, preferably 7 to 10% by weight, based on the total amount the second onion extract (B), wherein this amount refers to the weight of the dry onion extract, before dissolving this dry onion extract in the Solvent $S_3$.

Similar to the first onion extract (A), the second onion extract (B) is according to a further embodiment of the invention an onion extract which is obtained or obtainable by a process comprising an extraction, maceration or percolation of the onion material, either of fresh or dried onions, with a suitable solvent, preferably with the solvent $S_1$ described above, and a subsequent partial or preferably complete removal of the solvent. According to a preferred embodiment of the invention, after complete removal of the solvent, the remaining residue is re-dissolved in at least one suitable solvent, preferably in the above described solvent $S_3$. Optionally, the process for preparing the second onion extract (B) may comprise further steps, such as purification steps, in particular filtration steps.

The extraction, separation and evaporation steps are preferably carried out as already described above with regard to the preparation of the first onion extract (A).

Thus, according to a further embodiment, the second onion extract (B) is an onion extract (B). obtainable by a process comprising the steps
  (a) extracting fresh or dried onions, preferably *Allium cepa*, with a solvent $S_1$ comprising at least one alcohol to give a liquid phase $L_1$ and a solid residue $R_o$
  (b) separating the liquid phase $L_1$ from the solid residue $R_o$
  (c) evaporating the liquid phase $L_1$ to give a residue $R_1$
  ($d_B$) redissolving the residue $R_1$ in a solvent $S_3$ comprising at least one alcohol and water to give the onion extract (B).

According to yet another embodiment of the invention, the second onion extract (B) comprises the solvent $S_3$ in an amount in the range of from 98 to 85% by weight, preferably in the range of from 93 to 90% by weight, based on the total weight of the second onion extract (B). Further, the second onion extract (B) preferably comprises the residue $R_1$ in an amount in the range of from 2 to 15% by weight, preferably 7 to 10% by weight, based on the total weight of the second onion extract (B).

Thus, present invention also relates to a composition, as described above, wherein the composition comprises besides the first onion extract (A), additionally a second onion extract (B), wherein the second onion extract (B) is obtainable by a process comprising the steps
  (a) extracting fresh or dried onions, preferably *Allium cepa*, with a solvent $S_1$ comprising at least one alcohol to give a liquid phase $L_1$ and a solid residue $R_o$
  (b) separating the liquid phase $L_1$ from the solid residue $R_o$
  (c) evaporating the liquid phase $L_1$ to give a residue $R_1$
  ($d_B$) redissolving the residue $R_1$ in a solvent $S_3$ comprising at least one alcohol and water to give the onion extract (B)
wherein the onion extract (B) comprises $R_1$ in an amount in an amount of 2 to 15% by weight, based on the total weight of the onion extract (B).

Likewise, the present invention relates to a method for preparing a composition, as described above, and a composition obtainable or obtained by said method, wherein the composition comprises besides the first onion extract (A), additionally a second onion extract (B), wherein the second onion extract (B) is obtainable by a process comprising the steps
  (a) extracting fresh or dried onions, preferably *Allium cepa*, with a solvent $S_1$ comprising at least one alcohol to give a liquid phase $L_1$ and a solid residue $R_o$
  (b) separating the liquid phase $L_1$ from the solid residue $R_o$
  (c) evaporating the liquid phase $L_1$ to give a residue $R_1$
  ($d_B$) redissolving the residue $R_1$ in a solvent $S_3$ comprising at least one alcohol and water to give the onion extract (B)
wherein the onion extract (B) comprises $R_1$ in an amount in an amount of 2 to 15% by weight, based on the total weight of the onion extract (B).

According to a further embodiment, the second onion extract (B) consists of 2 to 15% by weight of residue $R_1$ and 85 to 98% by weight of the solvent $S_3$, preferably of 7 to 10% by weight of residue $R_1$ and 90 to 93% by weight of the solvent $S_3$, based on the total amount of the onion extract (B), with the sum of the amounts of $R_1$ and $S_3$ giving 100% by weight.

Preferably, the second onion extract (B) is not encapsulated in the liposomes.

Further Components

In general, the compositions of the invention may be formulated and provided in any suitable form which is advantageous and effective for consumer use. According to preferred embodiments, the compositions of the invention are in a form which is suitable for topical administration. Thus, the composition described is in particular formulated as solution, emulsion, suspension, or dispersion in suitable pharmaceutical bases or carriers, according to conventional methods known in the art for preparation of various dosage forms. Preferably the composition is a composition for topical applications which is formulated as gel, cream, paste, lotion, or ointment or as a similar vehicle suitable for topical administration. Topical administration may also be effected through the use of a dermal patch delivery system.

According to preferred further embodiment of the invention, the composition is a cream, an ointment, a gel or an emulsion. In particular the composition, described above, or the composition obtained or obtainable by the above described method, is a gel or an emulsion, most preferably a gel.

Besides the first onion extract (A), the liposomes and optionally the second onion extract (B), the composition described above, or the composition obtained or obtainable by the above described method may comprise one or more or more active agents and/or one or more cosmetically and/or pharmaceutically acceptable carrier or excipients.

The term "carrier or excipient" as used herein, means any suitable vehicle, which can be used to apply the present compositions to the skin in a safe and effective manner. A carrier may also reduce any undesirable side effects of the active compounds present in the composition. A suitable carrier is stable, i.e. e.g., incapable of reacting with other ingredients in the composition. The excipient and/or carrier must be "cosmetically and/or pharmaceutically acceptable" and "safe and effective" in the sense of being compatible with the other ingredients of the composition and not deleterious to the recipient thereof.

Examples of cosmetically and/or pharmaceutically acceptable excipients or carriers include stabilizers, thickeners, lubricants, waxes, film formers, surfactants, diluents, anti-oxidants, binders, preservatives, coloring agents (such as pigments or dyes), fragrances or emulsifiers. Cosmetically and/or pharmaceutically excipients may also include skin permeation enhancers.

In the following preferred active agents and cosmetically and/or pharmaceutically acceptable carriers and excipients are described:

Preservatives:

According to further embodiments of the invention the composition according to the invention comprises at least one preservative. According to further embodiments of the foregoing, the at least one preservative is selected from the group consisting of butylparaben; ethylparaben; Isobutylparaben, imidazolidinyl urea; methylparaben (Nipagen M); sorbic acid and its salts, O-phenylphenol; propylparaben; quaternium-14; quaternium-15; sodium dehydroacetate; Phenoxyethanol, Phenoxyisopropanol, Benzyl Alcohol, zinc pyrithione Triethylene Glycol, Propylene Glycol, Piroctone Olamine, Benzoic Acid, Silver Chloride, Titanium Dioxide, Diethylhexyl Sodium Sulfosuccinate, Diazolidinyl Urea, Iodopropynyl Butylcarbamate, Sodium DehydroacetatePotassium Sorbate, Disodium EDTA, Methylisothiazolinone, Phenylethylalcohol, Caprylyl Glycol, Capryloyl Glycine, Phenylpropanol, Methylpropanediol, Sodium Dehydroacetate Pentylene Glycol, 1,2 Hexanediol and their salts and their blends In general, the preservatives may be used in any amount which is effective to prevent or retard microbial growth.

According to yet a further embodiment, the total amount of preservatives used in the composition according to the invention ranges from 0.002 to 14% by weight, more preferably from 0.004 to 12% by weight, more preferably from 0.01 to 11% by weight, more preferably from 0.016 to 6% by weight, more preferably from 0.018 to 4% by weight, and even more preferably from 0.01 to 0.5 by weight, based on the total weight of the composition.

According to a further embodiment of the invention, the composition comprises methylparaben and/or sorbic acid, preferably methylparaben and Sorbic acid Thus, the present invention also relates to a composition, as described above, wherein the composition comprises Methylparaben and/or sorbic acid, preferably Methylparaben and sorbic acid. Likewise, the present invention relates to a method for preparing a composition, as described above, and a composition obtainable or obtained by said method, wherein the composition comprises Methylparaben and/or sorbic acid, preferably Methylparaben and Sorbic acid.

In case the composition comprises Methylparaben, the amount of Methylparaben used in the composition according to the invention ranges preferably from 0.001 to 3% by weight, more preferably from 0.002% to 2% by weight, more preferably from 0.005 to 1.5% by weight, more preferably from 0.008 to 1% by weight, more preferably from 0.009 to 0.5% by weight, and even more preferably from 0.01 to 0.2 by weight, based on the total weight of the composition.

In case the composition comprises sorbic acid, the amount of sorbic acid used in the composition according to the invention ranges preferably from 0.001 to 5% by weight, more preferably from 0.002% to 3% by weight, more preferably from 0.005 to 1.5% by weight, more preferably from 0.008 to 1% by weight, more preferably from 0.009 to 0.5% by weight, and even more preferably from 0.01 to 0.2 by weight, based on the total weight of the composition.

According to a further embodiment, the composition according to the invention comprises Methylparaben in an amount of 0.01 to 0.2% by weight and sorbic acid in an amount of 0.01 to 0.2% by weight, each based on the total weight of the composition.

Solubilizer:

According to further embodiments of the invention the composition according to the invention comprises at least one solubilizer. The solubilizer is e.g. a polyethylene glycol or polyethylene glycol derivative, more preferably polyethylene glycol.

In particular, the solubilizer is selected from the group consisting of PEG 200, PEG 300, PEG 400, PEG 600, PEG 1000, PEG 1450, PEG 3350, PEG 4000, PEG 6000, PEG 8000 and PEG 20000. Most preferably, the solubilizer is PEG 200.

According to further embodiments of the invention, in case the composition comprises at least one solubilizer, the total amount of solubilizers present ranges from 1 to 30% by weight, more preferably from 2 to 29% by weight, more preferably from 4 to 28% by weight, more preferably from 6 to 27% by weight, more preferably from 8 to 26% by weight, and even more preferably from 10 to 25 by weight, based on the total weight of the composition.

Thickener:

According to further embodiments of the invention, the composition according to the invention comprises at least one suitable thickener. Suitable thickeners are the swelling agents customarily used for gel formation in galenic pharmacy.

Examples of suitable thickeners include natural organic thickeners, such as agar-agar, gelatin, gum arabic, a pectin, and the like, modified organic natural compounds, such as carboxymethylcellulose or cellulose ethers, or fully synthetic organic thickeners, such as poly arylic compounds, vinyl polymers, or poly ethers.

In some embodiments, the excipient can increase the smoothness or other properties of the scar dressing formulation. Such additives include, but are not limited to glycerin, propylene glycol, butylene glycol, esters, diacyl glycerol esters, and starch.

Furthermore, the thickeners may be selected from algin; carbomers such as carbomer 934, 934P, 940 and 941; cellulose gum; cetearyl alcohol, cocamide DEA, dextrin; gelatin; hydroxyethylcellulose; hydroxypropylcellulose; hydroxypropyl methylcellulose; magnesium aluminum silicate; myristyl alcohol; oat flour; oleamide DEA; oleyl alcohol; PEG-7M; PEG-14M; PEG-9OM; stearamide DEA; stearamide MEA; stearyl alcohol; tragacanth gum; wheat starch; xanthan gum; wherein DEA is diethanolamine, and MEA is monoethanolamine. Alternatively or in addition thereto, thickeners used the composition of the present invention may comprise one or more of aluminum stearates; beeswax; candelilla wax; carnauba; ceresin; cetearyl alcohol; cetyl alcohol; cholesterol; hydrated silica; hydrogenated castor oil; hydrogenated cottonseed oil; hydrogenated soybean oil; hydrogenated tallow glyceride; hydrogenated vegetable oil; hydroxypropyl cellulose; lanolin alcohol; myristyl alcohol; octytdodecyl stearoyl sulfate; oleyl alcohol; ozokerite; microcystalline wax; paraffin, pentaerythrityl tetraoctanoate; polyacrylamide; polybutene; polyethylene; propylene glycol dicaprylate; propylene glycol dipelargonate; stearalkonium hectorite; stearyl alcohol; stearyl stearate; synthetic beeswax; trihydroxystearin; trilinolein; tristearin; zinc stearate; and the like.

According to further embodiments of the invention, the composition according to the invention comprises at least one thickener selected from the group consisting of polyacrylic acids and derivatives thereof, polysaccharides, such as xanthane gum, in particular Xantural 75, or alginates, carboxymethylcellulose or hydroxycarboxymethylcellulose, hydrocolloids such as gum Arabic or montmorillonite minerals, such as bentonites or fatty alcohols, polyvinyl alcohol and polyvinlypyrrolidone.

In particular, the composition according to the invention comprises a polysaccharide, preferably a xanthane gum, more preferably Xantural 75.

In case the composition comprises at least one thickener, the total amount of thickener used ranges preferably from 0.1 to 8% by weight, more preferably from 0.3% to 7% by weight, more preferably from 0.6 to 6% by weight, more preferably from 0.9 to 5% by weight, more preferably from 1.2 to 4% by weight, and even more preferably from 1.5 to 3% by weight, based on the total weight of the composition.

Preferably he composition comprises Xantural 75 in an amount in the range of from 0.1 to 8% by weight, more preferably from 0.3% to 7% by weight, more preferably from 0.6 to 6% by weight, more preferably from 0.9 to 5% by weight, more preferably from 1.2 to 4% by weight, and even more preferably from 1.5 to 3% by weight, based on the total weight of the composition.

Active Agents

The cosmetic compositions of the present invention may also comprise, besides the first onion extract (A) and optionally the second onion extract (B) at least one further active agent, in particular agents that sooth, condition and/or heal the skin.

The contained active agent may be selected from all active agents and mixtures thereof that can be applied to the surface of the skin. The active agent can act cosmetically or pharmaceutically. The active agent can be completely of plant origin or can be synthetic. The group of active agents may overlap with other groups of further ingredients described above and below, such as the thickening agents an the emulsifiers.

The at least one active agent of the invention is preferably selected from the group of substances having moisturizing and barrier strengthening properties, such as e.g. hydroviton, an emulation of NMF, chitosan, alginat, pyrrolidone carbonic acid and salts thereof, lactic acid and salts thereof, glycerol, sorbitol, propylene glycol and urea, substances of the group of proteins and protein hydrolysates, such as e.g. collagen, elastin as well as silk protein, substances of the group of glycose aminoglucanes, such as e.g. hyaluronic acid, of the group of carbohydrates, such as e.g. pentavitin that corresponds in its composition to the carbohydrate mixture of the human subcomeus layer and the group of lipids and lipid precursors such as for example ceramides. Further advantageous active agents in the sense of the present invention may be selected from the group of vitamins, such as e.g. panthenol, niacin, a-tocopherol and its esters, vitamin A as well as vitamin C. Moreover, active agents selected from the group of antioxidants e.g. galates and polyphenols may be used. Urea, hyaluronic acid and pentavitin are preferred substances.

It is further preferred that substances having skin soothing and regenerative action, such agents promoting wound healing, are employed as active agents, such as e.g. panthenol, panthenol derivatives (e.g., ethyl panthenol), hyaloronic acid, allantoin, bisabolol, dipotassium glycyrrhizinate and phytosteroles. Advantageous active agents in the sense of the present invention are also plants and plant extracts. These are e.g. algae, aloe, arnica, barber's rash, comfrey, birch, nettle, calendula, oak, ivy, witch hazel, henna, hop, chamomile, ruscus, peppermint, marigold, rosemary, sage, green tea, tea tree, horsetail, thyme and walnut as well as extracts thereof.

Further active agents are e.g. antibiotics and other agents promoting wound healing, e.g. growth factors, enzyme preparations and insecticides.

In yet a further embodiment of the invention, the composition according to the invention comprises as active agent a substance of the group of panthenol or a panthenol derivative and/or glycose aminoglucanes, in particular hyaluronic acid and/or panthenol, most preferably hyaluronic acid and panthenol According to preferred further more specific embodiments of the invention, the composition comprises panthenol in an amount in the range of from 0.1 to 10% by weight, more preferably from 0.1% to 9% by weight, more preferably from 0.1 to 8% by weight, more preferably from 0.1 to 7% by weight, more preferably from 0.1 to 6% by weight, and even more preferably from 0.1 to 5% by weight, and/or hyaluronic acid in an amount in the range of from 0.1 to 2% by weight, more preferably from 0.001% to 1.8% by weight, more preferably from 0.005 to 1.6% by weight, more preferably from 0.01 to 1.4% by weight, more preferably from 0.05 to 1.2% by weight, and even more preferably from 0.1 to 1% by weight, based on the total weight of the composition.

Fragrances:

The cosmetic composition according to the invention may also further comprise at least one fragrance and/or at least one coloring agent. Fragrances and/or coloring agents well known to those skilled in the art may be used in effective amounts to impart the desired fragrance and color to the compositions of the invention.

According to a preferred embodiment, the composition comprises at least one fragrance, in particular Parfume Oil Natura E, which is commercially available e.g. from Robertet GmbH, Germany.

The amount of the at least one fragrance, preferably the Parfume Oil Natura E, ranges according to further embodiments of the invention
from 0 to 2% by weight, more preferably from 0.01% to 1.8% by weight, more preferably from 0.02 to 1.6% by weight, more preferably from 0.03 to 1.4% by weight, more preferably from 0.04 to 1.2% by weight, and even more preferably from 0.05 to 1.0% by weight, based on the total weight of the composition.

Diluent:

According to a further embodiment of the invention, the composition according to the invention comprises at least one diluent, in particular purified, preferably in an amount of from 30% to 80% by weight, more preferably from 35 to 70% by weight, more preferably from 40 to 60% by weight, based on the total weight of the composition.

Optionally, the composition according to the invention comprises, additionally to the solvent $S_2$ and optionally $S_3$, at least one alcohol, preferably ethanol.

Emulsifier:

Optionally, the composition according to the invention comprises one or more emulsifiers. In particular, the emulsifiers (i.e., emulsifying agents) are preferably used in amounts effective to provide uniform blending of ingredients of the composition.

Preferred emulsifiers include one or more of
(i) anionics such as fatty acid soaps, e.g., potassium stearate, sodium stearate, ammonium stearate, and triethanolamine stearate; polyol fatty acid monoesters containing fatty acid soaps, e.g., glycerol monostearate containing either potassium or sodium salt; sulfuric esters (sodium salts), e.g., sodium lauryl 5 sulfate, and sodium cetyl sulfate; and polyol fatty acid monoesters containing sulfuric esters, e.g., glyceryl monostearate containing sodium lauryl surfate;

(ii) cationics chloride such as N(stearoyl colamino form-ylmethyl) pyridium; N-soya-N-ethyl morpholinium ethosulfate; alkyl dimethyl benzyl ammonium chloride; diisobutylphenoxytheoxyethyl dimethyl benzyl ammonium chloride; and cetyl pyridium chloride; and (iii) nonionics such as polyoxyethylene fatty alcohol ethers, e.g., monostearate; polyoxyethylene lauryl alcohol; polyoxypropylene fatty alcohol ethers, e.g., propoxylated oleyl alcohol; polyoxyethylene fatty acid esters, e.g., polyoxyethylene stearate; polyoxyethylene sorbitan fatty acid esters, e.g., polyoxyethylene sorbitan monostearate; sorbitan fatty acid esters, e.g., sorbitan; polyoxyethylene glycol fatty acid esters, e.g., polyoxyethylene glycol monostearate; and polyol fatty acid esters, e.g., glyceryl monostearate and propylene glycol monostearate; and ethoxylated lanolin derivatives, e.g., ethoxylated lanolins, ethoxylated lanolin alcohols and ethoxylated cholesterol. The selection of emulsifiers is exemplarily described in Schrader, Grundlagen and Rezepturen der Kosmetika, Huthig Buch Verlag, Heidelberg, $2^{nd}$ edition, 1989, $3^{rd}$ part.

Film Former:

Optionally the composition according to the invention may comprise a film former. In general, film formers which are used in accord with the invention preferably keep the composition smooth and even. Such formers include, but are not limited to, one or more of the following: acrylamide/sodium acrylate copolymer; ammonium acrylates copolymer; Balsam Peru; cellulose gum; ethylene/maleic anhydride copolymer; hydroxyethylcellulose; hydroxypropylcellulose; polyacrylamide; polyethylene; polyvinyl alcohol; pvm/MA copolymer (polyvinyl methylether/maleic anhydride); PVP (polyvinylpyrrolidone); maleic anhydride copolymer such as PA-18 available from Gulf Science and Technology; PVP/hexadecene copolymer such as Ganex V-216 available from GAF Corporation; and acryliclacrylate copolymer.

Waxes:

According to embodiments of the present invention which are further described, the composition comprises one or more waxes. Preferred waxes include one or more of the following: animal waxes, such as beeswax, and preferably hexadecanoic acid ester of tricontanol contained therein, spermaceti, or wool wax (lanolin); plant waxes, such as carnauba or candelilla; mineral waxes, such as montan wax or ozokerite; and petroleum waxes, such as paraffin wax and microcrystalline wax (a high molecular weight petroleum wax). Alternatively or in addition to these, one or more synthetic waxes may be used in the composition, wherein said one or more synthetic waxes preferably include polyethylene, polyoxyethylene, and hydrocarbon waxes derived from carbon monoxide and hydrogen, and combinations of two or more thereof.

In particular, preferred waxes which may be used in the composition of the present invention include one or more of cerosin; cetyl esters; hydrogenated joioba oil; hydrogenated jojoba wax; hydrogenated rice bran wax; Japan wax; jojoba butter; jojoba oil; jojoba wax; munk wax; montan acid wax; ouricury wax; rice bran wax; shellac wax; sufurized jojoba oil; synthetic beeswax; synthetic jojoba oils; trihydroxystearin; cetyl alcohol; stearyl alcohol; cocoa butter; fatty acids of lanolin; mono-, di- and triglycerides which are solid at 25° C., e.g., glyceryl tribehenate (a triester of behenic acid and glycerine) and C19-C36 acid triglyceride (a mixture of triesters of C19-C36 carboxylic acids and glycerine) available from Croda, Inc., New York, N.Y. under the tradenames Syncrowax HRC and Syncrowax HGL-C, respectively; fatty esters which are solid at 25° C.; silicone waxes such as methyloctadecaneoxypolysiloxane and poly (dimethylsiloxy) stearoxysiloxane; stearyl mono- and diethanolamide; rosin and its derivatives such as the abietates of glycol and glycerol; hydrogenated oils solid at 25° C.; and sucroglycerides.

According to one embodiment of the invention, the composition according to the invention, comprises besides the first onion extract (A) and the liposomes, optionally a second onion extract (B), at least one diluent, at least one solubilizer, at least one preservative, at least one thickener, at least one fragrance and at least one active agent.

According to a further embodiment of the invention, the composition described above, comprises besides the first onion extract (A) and the liposomes at least PEG, panthenol and Hyaluronic acid.

According to yet a further preferred embodiment, the composition according to the invention, comprises besides the first onion extract (A) and the liposomes, a second onion extract (B), purified water, PEG, in particular PEG 200, methylparabene and/or sorbic acid, a xanthane gum, at least one fragrance and panthenol and/or hyaluronic acid, more preferably the composition according to the invention, comprises, in particular consist of, the first onion extract (A), liposomes, a second onion extract (B), purified water, PEG, methylparabene, sorbic acid, a xanthane gum, at least one fragrance, panthenol and hyaluronic acid.

According to further embodiments of the invention, the composition according to the invention, comprises, the first onion extract (A) in an amount in the range of from 0.5 to 3% by weight, liposomes in an amount in the range of from 0.01 to 0.5% by weight, a second onion extract (B) in an amount in the range of from 5 to 15% by weight, purified water in an amount of from 40 to 60% by weight, PEG 200 in an amount of from 10 to 25% by weight, in an amount of 0.01 to 0.2% by weight and sorbic acid in an amount of from 0.01 to 0.2% by weight, Xantural 75 in an amount of from 1.5 to 3% by weight, a fragrance, in particular Parfume Oil Natura E, in an amount of from 0.05 to 1.0% by weight, panthenol in an amount of from 0.1 to 5% by weight and hyaluronic acid in an amount of from 0.1 to 1% by weight, based on the total weight of the composition.

According to yet further embodiments of the invention the composition according to the invention, consists of the first onion extract (A) in an amount in the range of from 0.5 to 3% by weight, liposomes in an amount in the range of from 0.01 to 0.5% by weight, a second onion extract (B) in an amount in the range of from 5 to 15% by weight, purified water in an amount of from 40 to 60% by weight, PEG 200 in an amount of from 10 to 25% by weight, in an amount of 0.01 to 0.2% by weight and sorbic acid in an amount of from 0.01 to 0.2% by weight, Xantural 75 in an amount of from 1.5 to 3% by weight, a fragrance, in particular Parfume Oil Natura E, in an amount of from 0.05 to 1.0% by weight, panthenol in an amount of from 0.1 to 5% by weight and hyaluronic acid in an amount of from 0.1 to 1% by weigh, and optionally minor amounts of ethanol, all amounts being based on the total weight of the composition, with the sum of the amounts of all components giving 100% by weight.

The Method for Preparing the Composition

According to an embodiment of the present invention, the composition according to the invention is prepared by providing a first onion extract (A), providing liposomes or membrane components capable of forming liposomes upon contact with the onion extract (A) and contacting of both components, thereby encapsulating at least a portion of the onion extract (A) into liposomes.

Thus, the present invention also relates to a method for preparing a composition comprising an onion extract (A), and liposomes, and a composition obtained or obtainable by said method, wherein at least a portion of the onion extract is encapsulated in the liposomes, the method comprising:
(i) providing an onion extract (A)
(ii) providing liposomes or membrane components capable of forming liposomes upon contact with the onion extract (A), and
(iii) contacting the onion extract (A) according to (i) with the liposomes or membrane components capable of forming liposomes upon contact with the onion extract (A) according to (ii), thereby encapsulating at least a portion of the onion extract (A) into liposomes.

The liposomes according to the invention can be produced in accordance with any method for the preparation of liposomes known to the person skilled in the art, for instance those disclosed in the book "Liposomes-a practical approach" published by R. C. New (Oxford University Press, 1990).

The liposomes can for example be produced by dissolving the membrane components, such as the phospholipids or lecithin, in an alcohol, such as ethanol. The resulting lipid solution may subsequently be added slowly to an aqueous composition, in particular water, the first onion extract or mixtures thereof.

The liposomes may then develop spontaneously or may be formed by subjecting the mixture to a mechanical force. For example, a wide variety of methods are currently used in the preparation of liposome compositions. These include, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, French pressure cell technique, controlled detergent dialysis, and others. See, e.g., Madden et al., Chemistry and Physics of Lipids, 1990. Liposomes may also be formed by various processes which require shaking or vortexing.

As used herein, the term "spontaneously formed" is intended to encompass that meaning known in the art, wherein the formation of the liposome requires the application of minimal or no mechanical force to the mixture of membrane components.

The liposomes may further be reduced in size by, stirring at high speed, high pressure filtration, ultrasound, extrusion and/or homogenization, until the desired particle size is obtained.

According to a further embodiment of the invention, in (ii) membrane components capable of forming liposomes upon contact with the onion extract (A) are provided and dissolved in at least one alcohol, particular an alcohol such as methanol, ethanol, isopropanol or propanol, most preferably in ethanol.

Thus, the present invention also relates to a method for preparing a composition comprising an onion extract (A), and liposomes, and a composition obtained or obtainable by said method, wherein at least a portion of the onion extract is encapsulated in the liposomes, the method comprising:
(i) providing an onion extract (A)
(ii) providing membrane components capable of forming liposomes upon contact with the onion extract (A), and dissolving these membrane components in at least one alcohol, particular an alcohol such as methanol, ethanol, isopropanol or propanol, most preferably in ethanol, giving a solution S(ii), and
(iii) contacting the onion extract (A) according to (i) with the solution S(ii), thereby forming liposomes and thereby encapsulating at least a portion of the onion extract (A) into said liposomes.

According to yet a further embodiment, in step (iii) the mixture comprising the onion extract (A) and the solution S(ii) is stirred and/or homogenized. The homogenization may be carried out, for example with a thorax mixer.

Optionally the onion extract (A) may be diluted with water prior to step (iii).

The term "membrane components capable of forming liposomes" refers to all naturally-derived or synthetic phospholipids or other surfactants, and optionally other membrane components already mentioned above, in particular to phospholipids or lecithin as described above.

Thus, the present invention also relates to a method for preparing a composition comprising an onion extract (A), and lecithin comprising liposomes, and a composition obtained or obtainable by said method, wherein at least a portion of the onion extract is encapsulated in the liposomes, the method comprising:
(i) providing an onion extract (A)
(ii) providing lecithin, and dissolving lecithin in at least one alcohol, particular an alcohol such as methanol, ethanol, isopropanol or propanol, most preferably in ethanol, giving a solution S(ii), and
(iii) contacting the onion extract (A) according to (i) with the solution S(ii), preferably stirring and/or homogenizing the resulting mixture, thereby forming lecithin comprising liposomes and thereby encapsulating at least a portion of the onion extract (A) into said liposomes.

It is to be understood that further additives may be added to solution S(ii), such as compounds which promote the formation of the liposomes and/or stabilize the liposomes after there formation.

The first onion extract (A) is preferably provided as described above.

In particular step (i) comprises the steps
(a) extracting fresh or dried onions, preferably *Allium cepa*, with a solvent $S_1$ comprising at least one alcohol to give a liquid phase $L_1$ and a solid residue $R_o$
(b) separating the liquid phase $L_1$ from the solid residue $R_o$
(c) evaporating the liquid phase $L_1$ to give a residue $R_1$
($d_A$) redissolving the residue $R_1$ in a solvent $S_2$ comprising at least one alcohol and water to give the onion extract (A), as described above. According to a preferred embodiment, the onion extract (A) comprises $R_1$ in an amount in an amount of 20 to 33% by weight, based on the total weight of the onion extract (A), as described above.

According to a further embodiment of the invention, the composition obtained according to step (iii) is optionally purified in one or more purification steps, and is subsequently mixed with a composition C1, said composition comprising one or more active agents and/or cosmetically and/or pharmaceutically acceptable carriers or excipients.

Thus, the present invention also relates to a method, as described above, and a composition obtainable by said method, the method further comprising
(iv) providing a composition (C1) comprising one or more active agents and/or cosmetically and/or pharmaceutically acceptable carriers or excipients
(v) mixing (C1) with the composition according to (iii).

In step (iv) the one or more active agents and/or cosmetically and/or pharmaceutically acceptable carriers or excipients are preferably contacted in one or more steps with at least one diluent, preferably with purified water to give the composition C1.

According to a further embodiment of the invention, the composition C1 comprises at least one diluent, at least one solubilizer, at least one preservative, at least one thickener, at least one fragrance and at least one active agent, and optionally a second onion extract (B).

According to further embodiments of the foregoing C1 comprises a second onion extract (B), purified water, PEG, in particular PEG 200, methylparabene and/or sorbic acid, a xanthane gum, at least one fragrance and panthenol and/or hyaluronic acid, more preferably C1 comprises a second onion extract (B), purified water, PEG, methylparabene, sorbic acid, a xanthane gum, at least one fragrance, panthenol and hyaluronic acid.

The composition C1 can in principle be prepared by combining all ingredients at suitable conditions known to those skilled in the art. In principle, any suitable order of adding the ingredients may be used.

According to one embodiment of the invention, step (iv) comprises dissolving and/or dispersing all active ingredients, if present, in a suitable diluent, preferably in purified water.

Thus, the present invention also relates to a method, as described above, and a composition obtainable by said method, the method further comprising
(iv) providing a composition (C1) comprising one or more active agents and/or cosmetically and/or pharmaceutically acceptable carriers or excipients, wherein the provision of the composition comprises
(a) dissolving and/or dispersing at least one active ingredient in a suitable diluents
(v) mixing (C1) with the composition according to (iii).

Optionally the resulting mixture obtained according to step (a) may be homogenized by suitable methods known to those skilled in the art. The homogenization may be carried out, for example with a static mixer and/or with a thorax mixer. In case the composition C1 comprises, for example panthenol and hyaluronic acid, the panthenol is preferably dissolved in water and the hyaluronic acid is added afterwards. Typically, the resulting mixture is stirred and/or homogenized until the hyaluronic acid is entirely swollen.

Thus, the present invention also relates to a method, as described above, and a composition obtainable by said method, the method further comprising
(iv) providing a composition (C1) comprising one or more active agents and/or cosmetically and/or pharmaceutically acceptable carriers or excipients, wherein the provision of the composition comprises
(a) dissolving panthenol in water, adding hyaluronic acid and stirring and/or homogenizing the resulting mixture
(v) mixing (C1) with the composition according to (iii).

In yet a further embodiment, in step (iv)(a) the resulting mixture comprising the active ingredients is stirred for a time in the range of from 5 min to 1 d, more preferably 15 min to 5 h, more preferably 45 min to 3 h, preferably at a temperature in the range of from 5 to 30° C., more preferably 20 to 28° C. During this step, the temperature may be varied or held essentially constant.

In case the composition C1 comprises at least one solubilizer and at least one preservative, the at least one preservative is preferably incorporated into the at least one solubilizer in a separate step (b). This "incorporation" is preferably achieved by stirring and/or homogenization.

Thus, the present invention also relates to a method, as described above, and a composition obtainable by said method, the method further comprising
(iv) providing a composition (C1) comprising one or more active agents and/or cosmetically and/or pharmaceutically acceptable carriers or excipients, wherein the provision of the composition comprises
(b) incorporating at least one preservative into at least one solubilizer
(v) mixing (C1) with the composition according to (iii).

Thus, the present invention also relates to a method, as described above, and a composition obtainable by said method, the method further comprising
(iv) providing a composition (C1) comprising one or more active agents and/or cosmetically and/or pharmaceutically acceptable carriers or excipients, wherein the provision of the composition comprises
(a) dissolving and/or dispersing at least one active ingredient in a suitable diluents
(b) incorporating at least one preservative into at least one solubilizer
(v) mixing (C1) with the composition according to (iii).

Preferably, in step (iv)(b), the mixture is stirred for a time in the range of from 5 min to 1 d, more preferably 15 min to 5 h, more preferably 45 min to 3 h, preferably at a temperature in the range of from 5 to 30° C., more preferably 20 to 28° C. During this step, the temperature may be varied or held essentially constant.

Preferably, subsequently, at least one thickener, if present, is added to the mixture comprising the least one preservative and the at least one solubilizer.

In case, the composition comprises a second onion extract (B), this onion extract is preferably mixed subsequently with the composition comprising the at least one solulibilizer and the at least one preservative. Preferably, the resulting mixture is stirred for a time in the range of from 5 min to 1 d, more preferably 15 min to 5 h, more preferably 45 min to 3 h, preferably at a temperature in the range of from 5 to 30° C., more preferably 20 to 28° C. During this step, the temperature may be varied or held essentially constant. The second onion extract (B) is preferably provided as described above.

Thus, the present invention also relates to a method, as described above, and a composition obtainable by said method, the method further comprising
(iv) providing a composition (C1) comprising one or more active agents and/or cosmetically and/or pharmaceutically acceptable carriers or excipients, wherein the provision of the composition comprises
(a) dissolving and/or dispersing at least one active ingredient in a suitable diluents
(b) incorporating at least one preservative into at least one solubilizer, adding at least one thickener, and optionally adding a second onion extract (B),
(v) mixing (C1) with the composition according to (iii).

According to a further embodiment, subsequently, the mixture according to step (iv)(a) and the mixture according to step (iv)(b), which optionally comprises the at least one thickener and/or the second onion extract (B), are mixed, wherein this mixing process may be carried out by any method known to those skilled in the art. Preferably, the resulting mixture is stirred and/or homogenized for a time in the range of from 1 min to 1 d, more preferably 5 min to 5 h, more preferably 10 min to 10 min, preferably at a temperature in the range of from 20 to 30° C., more preferably 22 to 28° C. During this step, the temperature may be varied or held essentially constant. Preferably this step is carried out at a pressure of 500 to 800 mbar. Optionally, if present, the at least one fragrance may be added.

Thus, the present invention also relates to a method, as described above, and a composition obtainable by said method, the method further comprising
(iv) providing a composition (C1) comprising one or more active agents and/or cosmetically and/or pharmaceutically acceptable carriers or excipients, wherein the provision of the composition comprises
(a) dissolving panthenol in water, adding hyaluronic acid and stirring and/or homogenizing the resulting mixture,
(b) incorporating at least one preservative into at least one solubilizer, adding at least one thickener, and optionally adding a second onion extract (B),
(c) mixing the mixtures according to (a) and (b), to give the composition C1,
(v) mixing (C1) with the composition according to (iii).

It is to be understood that the formulation of the composition preferably takes place under GMP standardized conditions in order to ensure quality, pharmaceutical security, and effectiveness of the medicament. Further criteria for an ingredient being pharmaceutically acceptable can be derived from approval regulations by a regulatory agency or other generally recognized pharmacopoeias.

The composition according to the present invention is preferably used in treating and/or preventing a scar.

The term "scar" is understood by the skilled person. As used herein, the term, preferably, refers to an abnormal morphological structure which results from a wound, in particular from wounds such as cuts, lacerations, abrasions, gunshot wounds, traumatic skin injury, penetration wounds, acne, operation wounds and burns. A scar typically comprises fibrous tissue.

Preferably, the term "scar" includes hypertrophic scars, atrophic scars, and keloid scars. Atrophic scars are flat and depressed below the surrounding skin as a valley or hole. Usually, they are caused when underlying structures which support the skin, e.g. fat tissue or muscle tissue are lost. Hypertrophic scars are elevated scars. Hypertrophic scars occur when the body overproduces collagen. Thereby, the scar is raised above the surrounding skin. Keloid scars are elevated scars that spread beyond the margins of the original wound and invade the surrounding normal skin in a way that is site specific, and often contain whorls of collagen arranged in an abnormal fashion. As laid out elsewhere herein, it particularly contemplated to treat scars shortly after scar formation. Moreover, it is preferred to treat scars which have been present over a longer period at the time at which treatment is initiated.

Moreover, the term "scar", preferably, also includes stretch marks. Stretch marks (frequently also referred to as striae) are a form of scarring caused by the overstretching of skin. This stretching disrupts the normal production of collagen and a scar results. Preferably, stretch marks are caused by rapid growth or rapid weight gain, in particular as a consequence of pregnancy. The term "stretch marks" preferably, includes striae distensae, striae atro phicans, striae rubra (red stretch marks) and striae alba (white stretch marks).

The terms "treating a scar" or "treatment of a scars", preferably, refers to the therapeutic treatment or the cosmetic treatment of a scar. The cosmetic treatment, preferably, comprises the administration of the composition of the present invention to a subject with a scar for improving the appearance of scar tissue and/or for reduction of scar tissue. The improvement of appearance of scar tissue, preferably, refers to reduced discoloration, decreased hyperpigmentation, softening of scar tissue, decreased erythema, or improved aesthetic appearance of the scar. The reduction of scar tissue, preferably, refers to reduced scar height and/or scar size.

Preferably, the terms "treating a scar" or "treatment of scars" comprise softening of scar tissue, i.e. and, thus, improving softness of scar tissue, improved aesthetic appearance of the scar, and, more preferably, reduced discoloration of the scar. Preferably, the discoloration of a scar is reduced if the redness of the scar is reduced. By reducing the discoloration, the scar becomes less visible.

As set forth above, the terms also refer to the therapeutic treatment of a scar, in particular include amelioration or prevention of pain (in particular scar pain) and amelioration of prevention of purities.

The term "subject" as used herein relates to animals, preferably mammals, and, more preferably, humans.

Preferably, the composition of the present invention is administered topically. More preferably, it is administered topically to the scar, i.e. to the scar tissue, or to the stretch mark. In particular, the composition shall be administered by spreading it on the scar or the stretch mark.

According to a further embodiment of the invention, the composition of the present invention is administered during the wound healing process. According to another embodiment of the invention, the composition of the present invention is administered after completion of the wound healing process. In particular, the composition can of the present invention can be administered shortly after scar formation, e.g. within one months after scar formation. Further, it is contemplated to treat older scars which have been present over a longer period at the time at which treatment is initiated. Thus, the scar, preferably, has been present for at least one month, more preferably, for at least six months, or, most preferably, for at least one year at the time at which treatment is initiated.

In yet further embodiments of the invention, the composition of the present invention is administered one to five times daily. More preferably, the composition of the present invention is administered three times daily. Even more preferably, the composition of the present invention is administered twice daily. Most preferably, the composition of the present invention is administered once daily.

It is to be understood that the composition of the present invention is administered in an effective amount, in particular in a therapeutically effective amount, i.e. in an amount which allows for the treatment or prevention of a scar. Whether an amount of the composition is effective or not can be determined by the skilled person without further ado.

The composition of the present invention can be also used for preventing scars, i.e. for preventing scar formation. The term "preventing" as used herein, preferably, refers to the administration the composition of the present invention to a subject in order to prevent or, in particular, to reduce de novo formation of scars. Moreover, the prevention of scars preferably, also, comprises the amelioration or prevention of pain and/or pruritus during scar formation. In order to prevent scars, the composition of the present invention is preferably, topically administered to a wound while the wound is still in the process of healing, and, thus, during completion of the wound healing process.

According to further embodiments of the invention, the composition of the present invention can be used for preventing the formation of stretch marks in subject. Preferably, said subject is a subject who is at risk of developing stretch marks. A subject who is at risk of developing stretch marks, is preferably, a rapidly growing teenager, or a bodybuilder. More preferably, said subject is a pregnant woman. In case, the composition of the present invention is used for preventing the formation of stretch marks, the composition is preferably administered to regions which are prone to developing stretch marks. E.g., if the subject is a pregnant woman, the composition is, preferably, administered to the abdomen.

According to further embodiments of the invention, the composition of the present invention, further exhibits a bactericidal activity. The term "bactericidal activity" as used herein, preferably refers to an activity which is capable killing bacterial cells. The composition of the present invention may, if administered to a subject, advantageously allow for treating and preventing scars and for killing bacterial cells in the scar tissue.

Also, the composition of the present invention may further prevent excessive fibroblast proliferation.

Moreover, the composition of the present invention, preferably, further exhibits anti-inflammatory activity.

The present invention also relates to a method for treating and/or preventing a scar in a subject in need thereof comprising administering to said subject a therapeutically effective amount of a composition of the present invention.

The present invention also relates to the use of the composition of the present invention for treating and/or preventing a scar in a subject in need thereof.

The present invention also relates to a method for the cosmetic treatment of a scar in a subject in need thereof comprising administering to said subject an effective amount of a composition of the present invention.

The present invention also relates to the use of the composition of the present invention for the cosmetic treatment of a scar in a subject in need thereof.

As set forth above cosmetic treatment, preferably, comprises the administration of the composition of the present invention to a subject with a scar for improving the appearance of scar tissue and/or for reduction of scar tissue. In particular, the term comprises softening of scar tissue, i.e. and, thus, improving softness of scar tissue, improved aesthetic appearance of the scar, and reduced discoloration of the scar—

In the following especially preferred embodiments of the present invention are described:

1. A composition comprising
    a first onion extract (A), and
    liposomes,
    wherein at least a portion of the first onion extract (A) is encapsulated in the liposomes.
2. The composition according to embodiment 1, wherein the liposomes are phospholipid comprising liposomes, preferably lecithin comprising liposomes.
3. The composition according to embodiment 1 or 2, wherein the liposomes have a diameter in the range of from 50 to 450 nm, preferably in the range of from 150 to 350 nm, measured with Photon Correlation Spectroscopy.
4. The composition according to any of embodiments 1 to 3 comprising the first onion extract (A) in an amount in the range of from 0.1-25 weight % based on the total weight of the composition.
5. The composition according to any of embodiments 1 to 4, wherein the first onion extract (A) comprises a solvent $S_2$, said solvent comprising at least one alcohol and water, preferably ethanol and water.
6. The composition according to any of embodiments 1 to 5, wherein the first onion extract (A) is an *Allium cepa* extract.
7. The composition according to any of embodiments 1 to 6, wherein the first onion extract (A) is obtainable by a process comprising the steps
    (a) extracting fresh or dried onions, preferably *Allium cepa*, with a solvent $S_1$ comprising at least one alcohol to give a liquid phase $L_1$ and a solid residue $R_o$
    (b) separating the liquid phase $L_1$ from the solid residue $R_o$
    (c) evaporating the liquid phase $L_1$ to give a residue $R_1$
    ($d_A$) redissolving the residue $R_1$ in a solvent $S_2$ comprising at least one alcohol and water to give the first onion extract (A)
    wherein the first onion extract (A) comprises $R_1$ in an amount of 20 to 33% by weight,], based on the total weight of the first onion extract (A).
8. The composition according to embodiment 7, wherein the at least one alcohol comprised in $S_1$ is ethanol, preferably wherein $S_1$ is an aqueous mixture comprising at least 70% by weight of ethanol, based on total weight of the solvent $S_1$.
9. The composition according embodiment 7 or 8, wherein the alcohol comprised in $S_2$ is ethanol, preferably wherein $S_2$ comprises ethanol in an amount in the range of from 5 to 25% by weight, and water in an amount of from 95 to 75% by weight, based on total weight of the solvent $S_2$.
10. The composition according to any of embodiments 1 to 9, wherein the composition further comprises one or more or more active agents and/or one or more cosmetically and/or pharmaceutically acceptable carrier or excipients.
11. The composition according to any of embodiments 1 to 10, wherein the composition further comprises a second onion extract (B), wherein the second onion extract (B) is obtainable by a process comprising the steps
    (a) extracting fresh or dried onions, preferably *Allium cepa*, with a solvent $S_1$ comprising at least one alcohol to give a liquid phase $L_1$ and a solid residue $R_o$
    (b) separating the liquid phase $L_1$ from the solid residue $R_o$
    (c) evaporating the liquid phase $L_1$ to give a residue $R_1$
    ($d_B$) redissolving the residue $R_1$ in a solvent $S_3$ comprising at least one alcohol and water to give the second onion extract (B) wherein the onion extract (B) comprises $R_1$ in an amount in an amount of 2 to 15 weight, based on the total weight of the second onion extract (B).
12. The composition according embodiment 11, wherein the alcohol comprised in $S_3$ is ethanol, preferably wherein $S_3$ comprises ethanol in an amount in the range of from 5 to 40% by weight and water in an amount of from 95 to 60% by weight, based on total weight of the solvent $S_3$.
13. The composition according to embodiment 11 or 12, wherein the second onion extract (B) is not encapsulated in liposomes.
14. The composition according to any of embodiments 1 to 13, wherein the composition is a cream, an ointment, a gel or an emulsion, preferably a gel or an emulsion.
15. The composition according to any of embodiments 1 to 14, comprising at least one diluent, at least one solubilizer, at least one preservative, at least one thickener, at least one fragrance and at least one active agent.

16. The composition according to any of embodiments 1 to 15, wherein the composition additionally comprises at least one compound selected from the group consisting of PEG, panthenol and hyaluronic acid.

17. The composition according to any of embodiments 1 to 16, wherein the composition comprises methylparaben, preferably in an amount in the range of from 0.01 to 0.2 by weight, based on the total weight of the composition.

18. The composition according to any of embodiments 1 to 17, wherein the composition comprises sorbic acid, preferably in an amount in the range of from 0.01 to 0.2 by weight, based on the total weight of the composition.

19. The composition according to any of embodiments 1 to 18, wherein the composition comprises panthenol, preferably in an amount in the range of from 0.1 to 5% by weight, based on the total weight of the composition.

20. The composition according to any of embodiments 1 to 19, wherein the composition comprises hyaluronic acid, preferably in an amount in the range of from 0.1 to 1% by weight, based on the total weight of the composition.

21. The composition according to any of embodiments 1 to 20 further comprising at least one diluent, in particular purified water, preferably in an amount of from 30 from 40 to 60% by weight, based on the total weight of the composition, wherein the composition optionally comprises additionally ethanol.

22. The composition according to any of embodiments 1 to 21, wherein the composition comprises Xantural 75, preferably in an amount in the range of from 1.5 to 3% by weight, based on the total weight of the composition.

23. The composition according to any of embodiments 1 to 22, comprising at least one fragrance, preferably Parfume Oil Natura E, wherein the amount of at least one fragrance preferably ranges from 0.05 to 1.0% by weight, based on the total weight of the composition.

24. The composition according to any of embodiments 1 to 23, consisting of the first onion extract (A) in an amount in the range of from 0.5 to 3% by weight, liposomes in an amount in the range of from 0.01 to 0.5% by weight, a second onion extract (B) in an amount in the range of from 5 to 15% by weight, purified water in an amount of from 40 to 60% by weight, PEG 200 in an amount of from 10 to 25% by weight, in an amount of 0.01 to 0.2% by weight and sorbic acid in an amount of from 0.01 to 0.2% by weight, Xantural 75 in an amount of from 1.5 to 3% by weight, a fragrance, in particular Parfume Oil Natura E, in an amount of from 0.05 to 1.0% by weight, panthenol in an amount of from 0.1 to 5% by weight and hyaluronic acid in an amount of from 0.1 to 1% by weigh, and optionally minor amounts of ethanol, all amounts being based on the total weight of the composition, with the sum of the amounts of all components giving 100% by weight.

25. A method for preparing a composition comprising a first onion extract (A), and liposomes, wherein at least a portion of the first onion extract is encapsulated in the liposomes, the method comprising:
   (i) providing a first onion extract (A)
   (ii) providing liposomes or membrane components capable of forming liposomes upon contact with the onion extract (A), and
   (iii) contacting the first onion extract (A) according to (i) with the liposomes or the membrane components capable of forming liposomes upon contact with the onion extract (A) according to (ii), thereby encapsulating at least a portion of the first onion extract (A) into liposomes.

26. The method according to embodiment 25, further comprising
   (iv) providing a composition (C1) comprising one or more cosmetically and/or pharmaceutically acceptable carriers or excipients
   (v) mixing (C1) with the composition according to (iii).

27. The method according to embodiment 25 or 26, wherein step (i) comprises
   (a) extracting fresh or dried onions, preferably *Allium cepa*, with a solvent $S_1$ comprising at least one alcohol to give a liquid phase $L_1$ and a solid residue $R_o$
   (b) separating the liquid phase $L_1$ from the solid residue $R_o$
   (c) evaporating the liquid phase $L_1$ to give a residue $R_1$
   ($d_A$) redissolving the residue $R_1$ in a solvent $S_2$ comprising at least one alcohol and water to give the first onion extract (A)
   wherein the first onion extract (A) comprises $R_1$ in an amount in an amount of 20 to 33% by weight, or 25-30% by weight, based on the total weight of the first onion extract (A).

28. A composition comprising an onion extract (A) (*Allium cepa*) and liposomes, obtainable by a method according to any of embodiments 25 to 27.

29. The composition according to embodiment 28, wherein the composition further comprises a second onion extract (B), wherein the second onion extract (B) is obtainable by a process comprising the steps
   (a) extracting fresh or dried onions, preferably *Allium cepa*, with a solvent $S_1$ comprising at least one alcohol to give a liquid phase $L_1$ and a solid residue $R_0$
   (b) separating the liquid phase $L_1$ from the solid residue $R_o$
   (c) evaporating the liquid phase $L_1$ to give a residue $R_1$
   ($d_B$) redissolving the residue $R_1$ in a solvent $S_3$ comprising at least one alcohol and
   water to give the second onion extract (B) wherein the onion extract (B) comprises $R_1$ in an amount in an amount of 2 to 15 weight, based on the total weight of the second onion extract (B).

30. The composition according embodiment 29, wherein the alcohol comprised in $S_3$ is ethanol, preferably wherein $S_3$ comprises ethanol in an amount in the range of from 5 to 25% by weight and water in an amount of from 95 to 75% by weight, based on total weight of the solvent $S_3$.

31. The composition according to embodiment 29 or 30, wherein the second onion extract (B) is not encapsulated in liposomes.

32. The composition according to any of embodiments 28 to 31, wherein the composition is a cream, an ointment, a gel or an emulsion, preferably a gel or an emulsion.

33. The composition according to any of embodiments 28 to 32, wherein the composition additionally comprises at least one compound selected from the group consisting of PEG, panthenol and hyaluronic acid.
34. The composition according to any of embodiments 28 to 33, wherein the composition comprises methylparaben, preferably in an amount in the range of from 0.01 to 0.2 by weight, based on the total weight of the composition.
35. The composition according to any of embodiments 28 to 34, wherein the composition comprises sorbic acid, preferably in an amount in the range of from 0.01 to 0.2 by weight, based on the total weight of the composition.
36. The composition according to any of embodiments 28 to 35, wherein the composition comprises panthenol, preferably in an amount in the range of from 0.1 to 5% by weight, based on the total weight of the composition.
37. The composition according to any of embodiments 28 to 36, wherein the composition comprises hyaluronic acid, preferably in an amount in the range of from 0.1 to 1% by weight, based on the total weight of the composition.
38. The composition according to any of embodiments 28 to 37 further comprising at least one diluent, in particular purified water, preferably in an amount of from 40 to 60% by weight, based on the total weight of the composition.
39. The composition according to any of embodiments 28 to 38, wherein the composition comprises Xantural 75, preferably in an amount in the range of from 1.5 to 3% by weight, based on the total weight of the composition.
40. The composition according to any of embodiments 28 to 39, comprising at least one fragrance, preferably Parfume Oil Natura E, wherein the amount of at least one fragrance preferably ranges from 0.05 to 1.0% by weight, based on the total weight of the composition.
41. The composition according to any of embodiments 1 to 24 or 28 to 40 for use in treating and/or preventing a scar.
42. The composition of embodiment 41, wherein said treating or preventing of a scar comprises the improving the appearance of scar tissue and/or for reduction of scar tissue.
43. The composition of embodiment 41 or 42, wherein said treating or preventing comprises softening the scar tissue or reducing discoloration of the scar.
44. The composition of any of embodiments 41 to 43, wherein the composition further prevents excessive fibroblast proliferation.
45. The composition of any of embodiments 41 to 44, wherein said composition is administered once a day.
46. The composition of any of embodiments 41 to 45, wherein said composition further exhibits a bactericidal activity.
47. The composition of any of embodiments 41 to 46, wherein said composition further exhibits anti-inflammatory activity.

The invention claimed is:

1. A method for treating a scar in a subject in need thereof, comprising topically administering once a day on the scar to treat the subject, an effective amount of a composition comprising:
   (a) an onion (*Allium cepa*) extract,
   (b) liposomes, have a unilamellar structure with a diameter in the range of from 50 to 450 nm as measured with Photon Correlation Spectroscopy, and
   (c) at least one compound selected from the group consisting of allantoin, hyaluronic acid and panthenol,
   wherein at least a portion of the onion extract is encapsulated in the liposomes, and
   wherein the composition is in the form of a gel.
2. The method of claim 1, wherein the liposomes are phospholipid comprising liposomes.
3. The method of claim 2, wherein the liposomes are lecithin comprising liposomes.
4. The method of claim 1, wherein the composition comprises the onion extract in an amount in the range of from 0.1-25 weight % based on the total weight of the composition.
5. The method of claim 1, wherein the onion extract comprises a solvent comprising at least one alcohol and water.
6. The method of claim 5, wherein the solvent comprises ethanol and water.
7. The method of claim 1, wherein the composition further comprises one or more or more active agents and/or one or more cosmetically and/or pharmaceutically acceptable carrier or excipients.
8. The method of claim 1, wherein the composition additionally comprises PEG.
9. The method of claim 1, wherein the method comprises improving the appearance of scar tissue and reduction of scar tissue.
10. The method of claim 1, wherein the method comprises softening the scar tissue or reducing discoloration of the scar.
11. The method of claim 1, wherein the method further prevents excessive fibroblast proliferation.

* * * * *